United States Patent [19]
Byrd et al.

[11] Patent Number: 5,620,001
[45] Date of Patent: *Apr. 15, 1997

[54] UNIVERSAL BLOOD-PRESSURE CUFF COVER

[76] Inventors: Timothy N. Byrd; Janice A. Byrd, both of 1267 Old Cades Cove Rd., Townsend, Tenn. 37882

[ * ] Notice: The term of this patent shall not extend beyond the expiration date of Pat. No. 5,228,448.

[21] Appl. No.: 233,060

[22] Filed: Apr. 26, 1994

[51] Int. Cl.$^6$ .................................................. A61B 5/022
[52] U.S. Cl. ........................................... 128/686; 606/202
[58] Field of Search ..................................... 128/677, 686, 128/849, 856; 606/201-3; 607/111

[56] References Cited

U.S. PATENT DOCUMENTS

| | | |
|---|---|---|
| 2,244,871 | 6/1941 | Guinzburg . |
| 2,911,974 | 11/1959 | Spence ................................. 607/111 X |
| 2,949,914 | 8/1960 | Waldrum ................................. 607/111 |
| 3,473,525 | 10/1969 | Hanafin . |
| 3,824,998 | 7/1974 | Snyder ................................. 128/856 X |
| 3,934,582 | 1/1976 | Gorrie ..................................... 128/856 |
| 4,197,944 | 4/1980 | Catlin . |
| 4,334,611 | 6/1982 | Watson et al. . |
| 4,378,009 | 3/1983 | Rowley et al. . |
| 4,406,281 | 9/1983 | Hubbard et al. . |
| 4,548,249 | 10/1985 | Slaughterbeck ..................... 128/686 X |
| 4,549,550 | 10/1985 | Kami . |
| 4,572,173 | 2/1986 | Comeau . |
| 4,905,715 | 3/1990 | Johnson . |
| 4,911,151 | 3/1990 | Rankin et al. . |
| 4,967,758 | 11/1990 | Masciarotte ............................. 128/686 |
| 4,979,953 | 12/1990 | Spence ................................. 128/686 X |
| 5,201,758 | 4/1993 | Glover ................................. 128/686 X |
| 5,228,448 | 7/1993 | Byrd ....................................... 128/677 |

FOREIGN PATENT DOCUMENTS

15450  8/1988  United Kingdom .

Primary Examiner—Angela D. Sykes
Attorney, Agent, or Firm—Pitts & Brittian, P.C.

[57] ABSTRACT

A universal blood-pressure cuff cover (10) for protecting the blood-pressure cuff of a sphygmomanometer. The protective cover (10) includes a top band (32) for being releasably received about the appendage of a patient and around the blood-pressure cuff (22) secured about such appendage. The top band (32) is fabricated of a flexible material and defines opposite edge portions (38 and 40) for being positioned on opposite sides of the blood-pressure cuff (22), and the opposite edge portions (38 and 40) are provided with draw members (46) for drawing together the flexible material of the top band (32) proximate the edge portions (38 and 40) and for biasing such edge portions toward the appendage of the patient.

19 Claims, 5 Drawing Sheets

UNIVERSAL BLOOD-PRESSURE CUFF COVER

TECHNICAL FIELD

This invention relates protective cover for a blood-pressure cuff which prohibits contaminants from being communicated between a blood-pressure cuff and a patient. In this particular invention the protective cover includes top band which is received about the blood-pressure cuff as it is secured about the appendage of a patient.

BACKGROUND ART

It is known in the medical community that significant bacterial colonization occurs on surfaces of non-disposable sphygmomanometer cuffs, more commonly referred to as blood-pressure cuffs, as well as on reused disposable cuffs. Contamination of blood-pressure cuffs can be particularly problematic in hospital intensive care units and emergency rooms where the cuffs are commonly exposed to blood and other bodily fluids, thus making the cuffs a possible source of infection if reused. With the increasing recognition that contamination of blood-pressure cuff can be a source of infection, it has been recommended that, where possible, a sterilized cuff, or an unused disposable cuff, be dedicated to each patient upon arrival at a hospital and that the cuff follow the patient around in the hospital. However, dedicating a cuff to each patient requires a large number of cuffs, thereby making the practice expensive. Moreover, it is procedurally difficult to insure that the cuff follows the patient's movements in the hospital. Disposable cuffs are available as a possible solution, but disposable cuffs also lead to substantial additional expense. Consequently persons working in the medical field still commonly reuse blood-pressure cuffs on different patients without cleaning the cuffs between patients.

In U.S. Pat. No. 5,228,448 ("the '448 Patent) a protective cover for a blood-pressure cuff is disclosed which reduces the possibility of contaminates being transmitted between a blood-pressure cuff and a patient. The protective cover of this patent includes a protective sheet defining an elongated bottom band joined by an intermediate portion to an elongated top band. The bottom band is wrapped about the appendage of a patient, and the blood-pressure cuff is wrapped about the bottom band. The top band is then pivoted relative to the bottom band at the intermediate portion over the blood-pressure cuff and wrapped thereabout. Whereas the cover of the '448 Patent represented a considerable advancement of the art, with this protective cover contaminates can still be communicated between the patient and cuff at the opposite edges of the cover. For example, where a patient is loosing blood or other bodily fluids the cover does not prevent such fluids from being communicated between the top and bottom bands at the edges of such bands. The cover of the '448 patent also restricts the positioning of the pneumatic tubes which communicate with the gauge and pump of the sphygmomanometer, and due to the manner in which such tubes exit the cover, movement of the patient can result in the cover being pulled out of position. Further, if the top band of the cover is tightly secured over the cuff so as to most advantageously prevent contamination of the cuff it can interfere with the proper inflation of the cuff and cause inaccurate blood pressure readings.

Other covering devices are shown in U.S. Pat. Nos. 4,911,151; 4,905,715; 4,572,173; 4,406,281; 4,378,009; 3,473,525; 2,244,871 and 15,450.

Therefore, it is an object of the present invention to provide an improved blood-pressure cuff cover which prohibits contaminates from being communicated between a patient and a blood-pressure cuff, and which can be universally used with blood-pressure cuffs of various sizes.

It is an object of the present invention to provide an improved blood-pressure cuff cover which protects health care workers from coming into contact with contaminated blood-pressure cuffs.

It is another object of the present invention to provide a blood-pressure cuff cover which does not restrict the positioning of the pneumatic tubes which communicate with the gauge and pump of the sphygmomanometer, and which will remain in the desired protective position notwithstanding movement of the patient.

Yet another object of the present invention is to provide a blood-pressure cuff cover which is easy to use and inexpensive to manufacture.

Still another object of the present invention is to provide a blood-pressure cuff cover which does not affect the accuracy of a sphygmomanometer.

DISCLOSURE OF THE INVENTION

Other objects and advantages will be accomplished by the present invention which provides a universal blood-pressure cuff cover for protecting the cuff of a sphygmomanometer. The protective cover includes a bottom band for being releasably received around an appendage of a patient, such as an arm or a leg. The blood-pressure cuff is releasably received around the bottom band such that the bottom band forms a protective barrier between the appendage and the blood-pressure cuff. The protective cover also includes a top band for being releasably received about the appendage of the patient and around the blood-pressure cuff secured about the bottom band. The top band is fabricated of a flexible material and defines first and second opposite edge portions for being positioned on opposite sides of the blood-pressure cuff. Further, the first and second opposite edge portions are provided with draw members for drawing together the flexible material of the top band proximate the first and second edge portions and for biasing the first and second edge portions toward the appendage of the patient thereby securing the first and second edges of the top band against the bottom band.

BRIEF DESCRIPTION OF THE DRAWINGS

The above mentioned features of the invention will be more clearly understood from the following detailed description of the invention read together with the drawings in which.

BEST MODE FOR CARRYING OUT THE INVENTION

Figure 1:
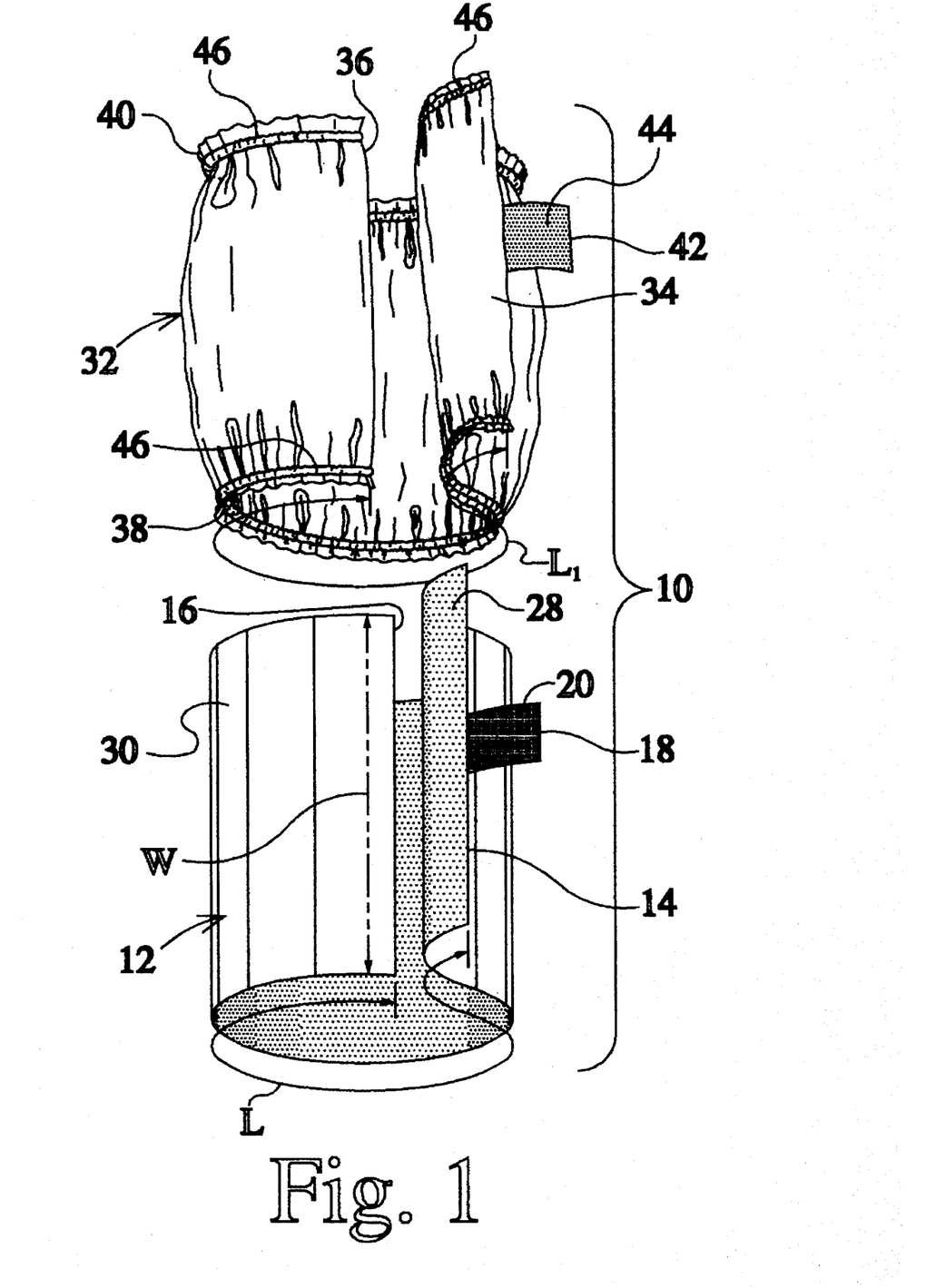
FIG. 1 illustrates a perspective view of the blood-pressure cuff cover of the present invention.

A universal blood-pressure cuff cover incorporating various features of the present invention is illustrated generally at 10 in FIG. 1. More specifically, the protective coverage is designed to cover the cuff of a sphygmomanometer utilized for measuring the blood-pressure of a patient, and to prevent the cuff from becoming contaminated during use and/or to protect the patient from being contaminated by the cuff. It will be recognized by those skilled in the art that during the blood-pressure measuring process such sphygmomanometer cuffs are releasably received about a patient's appendage, such as the patient's arm or leg, and inflated. As is set forth in detail below the protective cover 10 of the present invention places a protective layer of material about the cuff such that contaminates are prevented from contacting the cuff, and such that the cuff does not come into direct contact with the patient.

In one preferred embodiment the protective cover 10 includes a bottom band 12 having first and second opposite end portions 14 and 16, respectively, for being received about the appendage of a patient at the location where the blood-pressure cuff is to be secured. For example, in FIG. 2A the bottom band 12 is illustrated as being received about the arm of a patient. In this regard, the length L (see FIG. 1) of the bottom band 12 should be sufficient to allow the bottom band 12 to completely wrap around the appendage with the opposite end portions 14 and 16 of the bottom band 12 substantially overlapping, as illustrated in FIG. 2B. For example, a typical length L for the bottom band 12 is 18 inches.

The bottom band 12 is also provided with a securing mechanism for securing the bottom band 12 in position about the appendage of the patient. In the preferred illustrated embodiment the securing mechanism comprises an adhesive strip 18 defining an adhesive surface 20 which is provided on, and extends beyond, the first end portion 14 of the bottom band 12. As illustrated in FIG. 2B, after the bottom band 12 has been wrapped around the appendage, the adhesive strip 18 is secured to the adjacent material of the bottom band 12 to secure the position of the bottom band 12 on the appendage. Of course, other suitable securing mechanisms can be used to secure the bottom band 12 in position on the appendage, and the adhesive strip 18 is simply illustrative of one preferred means.

Figure 2A:
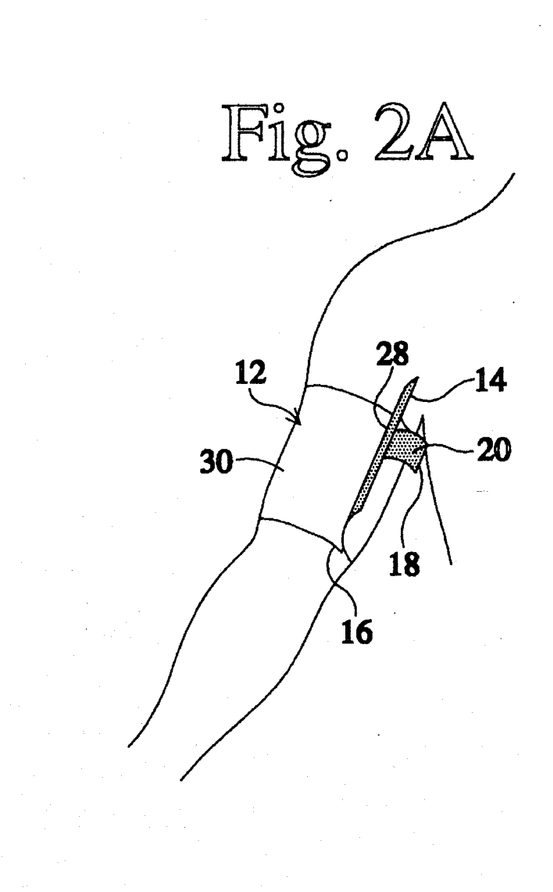
FIG. 2 illustrates a perspective view of the bottom band of a blood-pressure cuff cover of the present invention being secured on the arm of a patient.
Figure 2B:
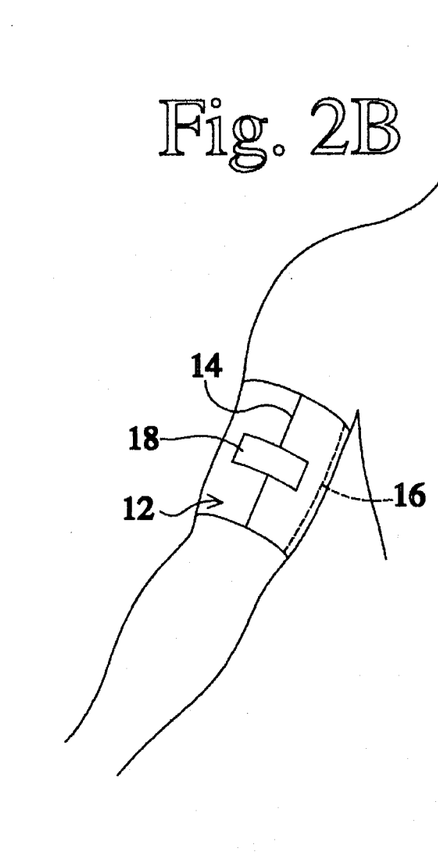
FIG. 2B illustrates a perspective view of the bottom band of a blood-pressure cuff cover of the present invention after it has been secured on the arm of a patient.
Figure 2C:
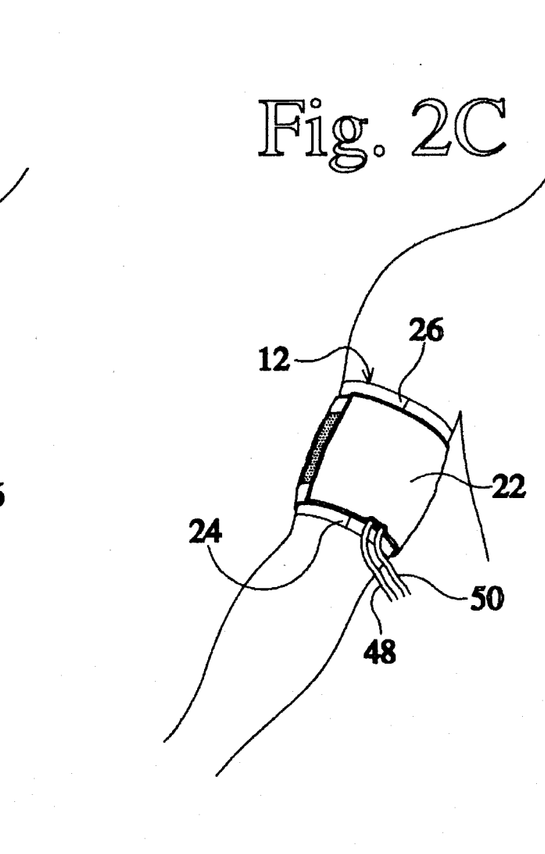
FIG. 2C illustrates a perspective view of a blood-pressure cuff secured about the bottom band of a blood-pressure cuff cover of the present invention.
Figure 2D:
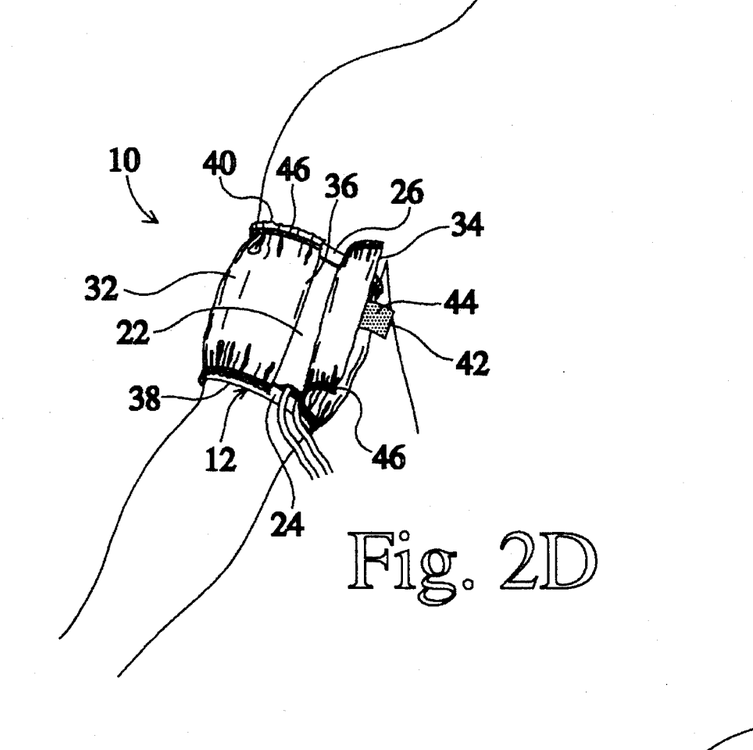
FIG. 2D illustrates a perspective view of the top band of a blood-pressure cuff cover of the present invention being secured over a blood-pressure cuff.

As illustrated in FIG. 2C, after the bottom band 12 is secured about the appendage of the patient, a blood pressure cuff 22 is secured over the bottom band 12. It will be noted that the width W (see FIG. 1) of the bottom band 12 is preferably greater than the width of the blood-pressure cuff 22. As a result, when the cuff 22 is applied over the bottom band 12 and substantially centered between the opposing edges of the bottom band 12 as illustrated in FIG. 2C, marginal areas 24 and 26 of the bottom band 12 are exposed on either side of the cuff 22.

The bottom band 12 of the protective cover 10 is preferably fabricated of a light, flexibly material which is substantially fluid impervious. In this regard, in the illustrated embodiment the bottom band 12 is fabricated of a two-ply material, having a first layer 28 of a soft, absorbent material and a thin second layer 30 of relatively soft, flexible, plastic film which is substantially fluid impervious. One suitable two-ply material is a spun bond polypropylene with film, currently being sold by Poly-Bond, Inc., of Charlotte, N.C. This Poly-Bond tissue has the desired fluid impervious qualities and is inexpensive, such that the protective cover 10 can be cost effectively used as a disposable item.

As best illustrated in FIG. 2A, the bottom band 12 is applied to the appendage such that the soft absorbent first layer 28 engages the skin of the patient. The placing of the soft first layer 28 against the patient's skin enhances the comfort of the patient and resists slippage of the bottom band 12 on the skin surface. The second layer 30 engages the cuff 22 and forms a fluid impervious barrier between the skin of the appendage and the surface of the cuff 22. Accordingly, contaminates on the cuff 22 cannot be communicated to the skin surface, and contaminates on the patient's skin cannot be communicated to the cuff 22.

With respect to the configuration of the bottom band 12, it will be appreciated that the length, width and configuration of the bottom band 12 can vary greatly as long as the bottom band 12, when received about the appendage, covers the entire area of the appendage about which the blood-pressure cuff is to be received. Accordingly, the rectilinear configuration of the preferred illustrated embodiment of the bottom band 12, and preferred lengths and widths thereof discussed above, are merely illustrative of one preferred embodiment of the bottom band.

As illustrated in FIG. 1, the blood-pressure cuff cover 10 also includes top band 32 which is receive about the appendage of the patient and the cuff 22. The top band 32 defines first and second end portions 34 and 36, respectively, and first and second opposite edge portions 38 and 40, respectively. The top band 32 of the protective cover 12 is preferably fabricated of a light, flexibly material which is dissolvable and substantially fluid impervious. In this regard, in the preferred embodiment the top band 32 is fabricated of a dissolvable, fluid impervious film, such as OREX, manufactured by Isulyser Company, Inc., of Norcross, Ga.

Figure 2E:
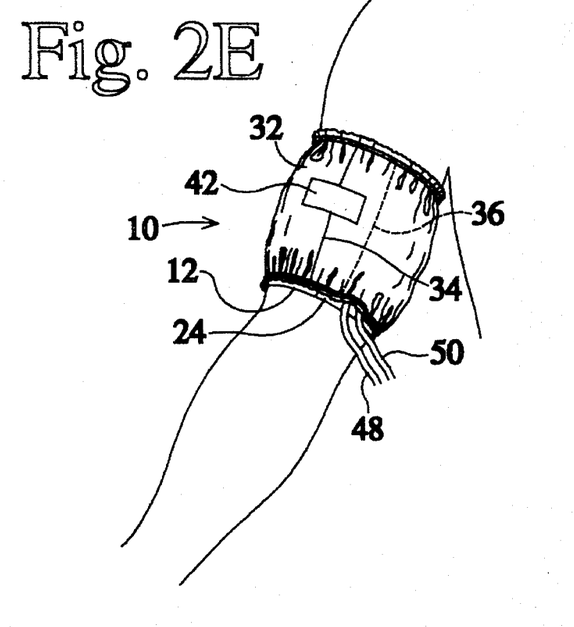
FIG. 2E illustrates a perspective view of the blood-pressure cuff cover of the present invention secured on the arm of a patient.

In FIG. 2C the top band 32 is illustrated as being received about the bottom band 12 of a protective cover 10 and a cuff 22, both of which have been secured about the arm of a patient. In this regard, the length $L_1$ (see FIG. 1) of the top band 32 should be sufficient to allow the top band 32 to completely wrap around the appendage, and the cuff secured thereon, with the opposite end portions 34 and 36 of the top band 32 substantially overlapping, as illustrated in FIG. 2E.

The top band 32 is also provided with a securing mechanism for securing the top band 32 in position about the appendage of the patient and about the cuff 22. In the preferred illustrated embodiment the securing mechanism comprises an adhesive strip 42 defining an adhesive surface 44 which is provided on, and extends beyond, the first end portion 34 of the top band 32. As illustrated in FIG. 2E, after the top band 32 has been wrapped around the cuff 22, the adhesive strip 42 is secured to the adjacent material of the top band 32 to secure the position of the top band 32 about the cuff 22. Of course, other suitable securing mechanisms can be used to secure the top band 32 in position and the adhesive strip 42 is simply illustrative of one preferred mechanism.

At the first and second edge portions 38 and 40 the top band 32 is provided with draw members 46 which draw together the material of the top band 32 proximate the first and second edge portions 38 and 40, respectively, and draw the edge portions 38 and 40 tightly about the appendage of the patient proximate the marginal areas 24 and 26, respectively, of the bottom band 12. In one preferred embodiment the draw members 46 define lengths of elastic which are secured along at least a substantial portion of the edge portions 38 and 40. (See FIG. 3). It will be recognized that the longitudinal bias of the draw members 46 serves to draw the material at the edge portions 38 and 40 together, and, when the top band 32 is secured over the cuff 22, such longitudinal biasing serves to bias the edge portions 38 and 40 of the top band 32 into engagement with the marginal areas 24 and 26, respectively, of the bottom band 12, thereby sealing the cuff 22 between the bottom band 12 and the top band 32.

Figure 3:
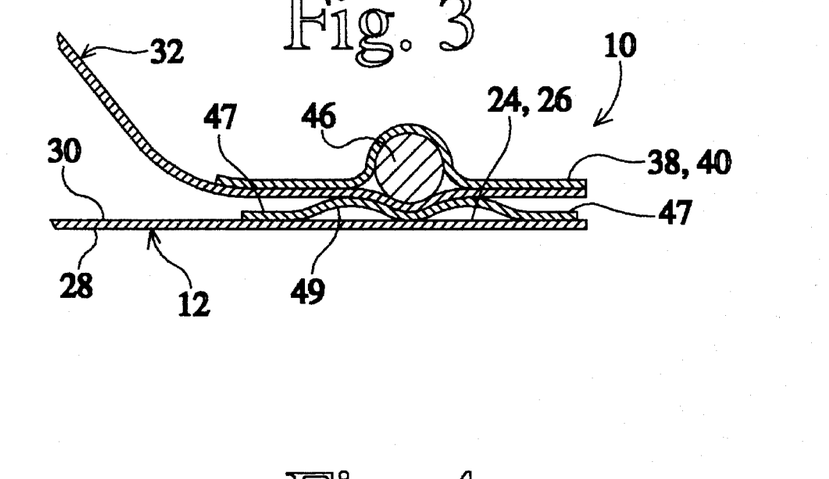
FIG. 3 illustrates a partial side elevation view, in section, of a blood-pressure cuff cover of the present invention.

Referring to FIG. 3, it will be noted that, if desired, the edge portions 38 and 40 of the top band 32 can be provided with absorbent strips 47 which are secured to and extend along the lower surface of the top band 32 proximate the edge portions 38 and 40. The absorbent strips 47 serve to absorb contaminating fluids, such as blood or other bodily fluids, and prohibit such contaminates from flowing under the edge portions 38 and 40, thereby reducing the likelihood of contaminates traveling into, or out of, the protective cover 10. Further, the absorbent strips 47 can be provided with adhesive surfaces 49 for engaging the marginal areas 24 and 26, if desired, in order to enhance the seal between the top and bottom bands.

Figure 4:
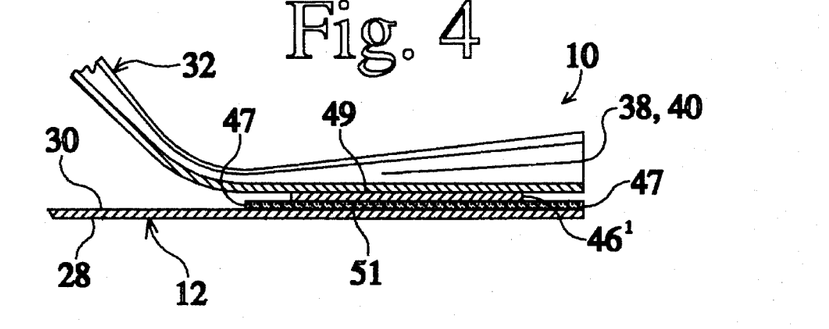
FIG. 4 illustrates a partial side elevation view, in section, of an alternate embodiment of a blood-pressure cuff cover of the present invention.

Of course, the lengths of elastic which comprise the draw members 46 of the protective cover 10 of FIGS. 1–3 are merely illustrative of one preferred embodiment. As illustrated in FIG. 4 at 46', the draw members can comprise an elastic tape which is secured along at least a substantial portion of the edge portions 38 and 40. (See FIG. 4). The upper surface 49 of the elastic tape 46' is provided with an adhesive which secures the tape 46' to the gathered material of the top band 32. Further, the lower surface 51 of the elastic tape 46' is preferably provided with an adhesive for securing the absorbent strip 47 to the top band 32. Suitable materials for the elastic tape 46' are the double-sided elastic tapes sold by 3-M Corporation of St. Paul, Minn., under product Nos. 1509 and 9920. However, other suitable elastic band material can be used.

Figure 5:
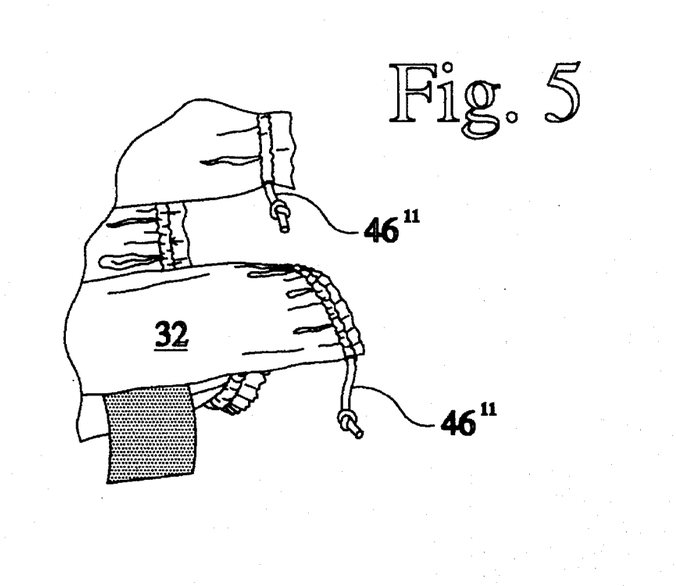
FIG. 5 illustrates a partial perspective view of an alternate embodiment of the blood-pressure cuff cover of the present invention.

Further, as illustrated in FIG. 5 at the draw members can comprise draw strings which are slidably received in a hem or opening along the edge portions 38 and 40 of the top band 32. It will be understood that when the top band 32 of the cover 10 is received over the cuff 22 the opposite ends of each of the draw strings 46" are secure together, thereby bringing the edge portions 38 and 40 of the top band 32 into engagement with the marginal areas 24 and 26, respectively, of the bottom band and sealing the cuff 22 between the bottom band 12 and the top band Of course, the top band 32 forms a protective barrier over the cuff 22 which prohibits outside contaminates from reaching the cuff, and prohibits contaminates on the cuff 22 from being communicated to the patient or those attending the patient. In this regard, since the draw members 46 serve to bring the edges of the top and bottom bands and 32 together, contaminates are prohibited from traveling between the interior and exterior of the cover 10 at the edges of the top and bottom bands 12 and 32.

It will be noted that the gathering of the material of the top band 32 at the edge portions 38 and 40 causes a blousing of the material of the top band 32 between the edge portions 38 and 40. This blousing of the material of the top band 32 insures that ample room is provided within the top band 32 to allow for the inflation of the cuff 22 without compromising the seal between the top and bottom bands 32 and 12 which is formed by the edge portions 38 and 40. Accordingly, the protective cover be does not interfere with the operation of the sphygmomanometer.

Further, the pneumatic tubes 48 and 50 which are operatively associated with the sphygmomanometer can be routed out of the protective cover be at any point along the edge portions 38 and 40. Accordingly, the tubes 48 and 50 can be placed in positions which are convenient to the doctor or other care giver. Also, the protective cover 10 and cuff 22 can remain secured on a patient between uses of the sphygmomanometer, and due to the blousing of the material of the top band 32, the tubes 48 and 50, and the gauge and pump (not shown) of the sphygmomanometer, can be stored in the top band 32 such that are out of the way, but ready for subsequent use.

It will be recognized by those skilled in the art that the top band 32 can be used without the bottom band 12 if desired. Used alone, the top band 32 still serves to cover the cuff 22 and protect the cuff from contamination. However, it will be understood that it is generally preferable to use the top band 32 in conjunction with some type of barrier between the skin of the appendage and the cuff whether it be the illustrated bottom band 12 or some other barrier means. Also, it is contemplated that the top band 32 can be provided with only one draw member 46 (46', 46") proximate the edge portion 40. However, it is preferable to provide a draw member proximate both edge portions 38 and 40.

Figure 6:
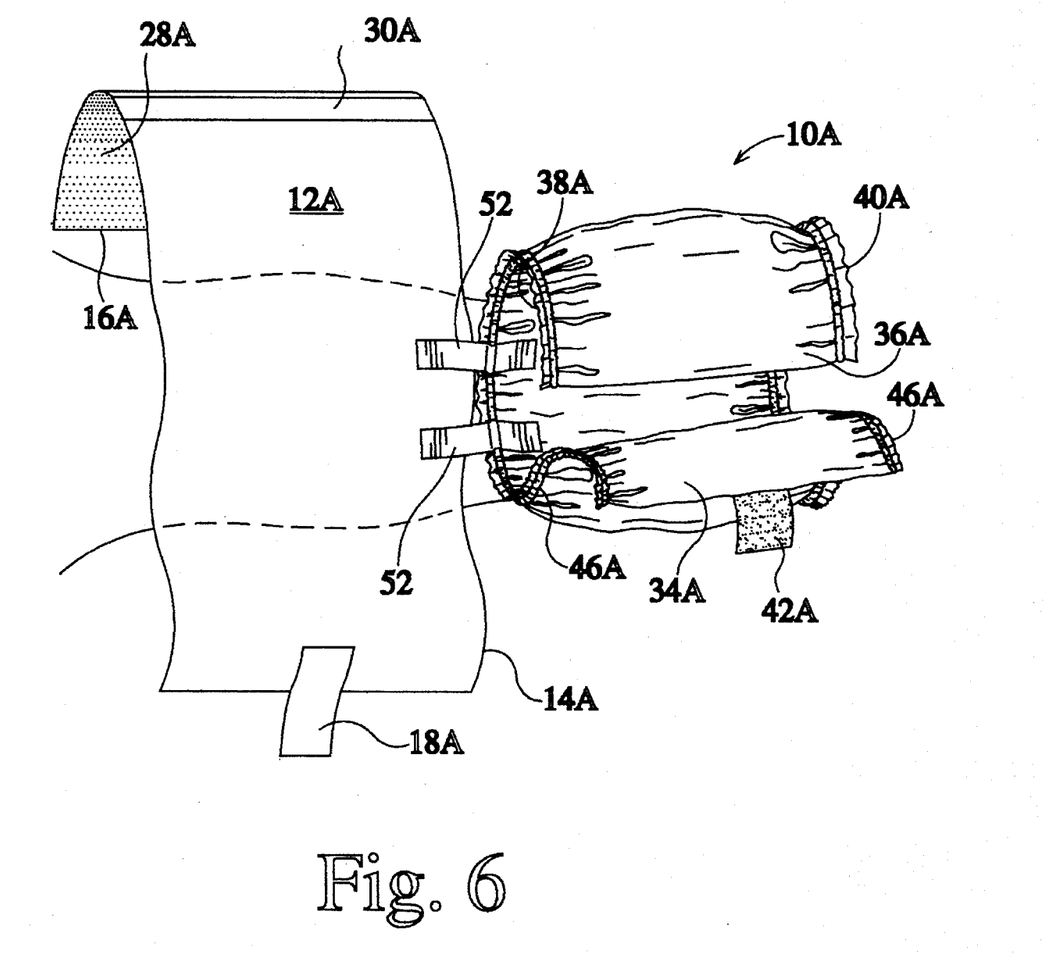
FIG. 6 illustrates a perspective view of a further alternate embodiment of the blood-pressure cuff cover of the present invention.

In FIG. 6 an alternate embodiment of the protective cover of the present invention is illustrated at 10A. Features and components of the protective cover 10A which are common to the above-described protective cover 10 are referenced by common numerals followed by the alphabetic character "A".

As illustrated in FIG. 6, the top band 32A and bottom band 12A of the protective cover 10A are connected by at least one, and preferably two, connecting members 52. In the preferred embodiment the connecting members 52 comprise adhesive strips. However, the connecting members 52 can be integrally formed with the bands 12A and 32A if desired. When the protective cover 10A is used, the first layer 28A of the bottom band 12A is placed against the skin of the appendage, and the bottom band 12A is wrapped around the appendage and secured with the adhesive strip 18A. The cuff is then be secured about the bottom band 12A as discussed with respect to the protective cover 10 described above. The top band 32A is then folded back over the cuff and secured in place with the adhesive strip 42A.

In light of the above it will be recognized that the present invention provides a protective cover for a blood-pressure cuff having great advantages over the prior art. The protective cover effectively prevents contaminates from being communicated between a patient and a blood-pressure cuff, and the cover is easy to use and inexpensive to manufacture.

Further, the cover of the present invention does not restrict the positioning of the pneumatic tubes which communicate with the gauge and pump of the sphygmomanometer, and remains in the desired protective position notwithstanding movement of the patient. Moreover, due to its bloused top band the protective cover does not adversely affect the accuracy of a sphygmomanometer.

While a preferred embodiment has been shown and described, it will be understood that there is no intent to limit the invention to such disclosure, but rather it is intended to cover all modifications and alternate constructions falling within the spirit and scope of the invention as defined in the appended claims.

We claim:

1. A blood-pressure cuff cover, said cover comprising a top band for being releasably received about the appendage of a patient and around a blood-pressure cuff secured about the appendage, said top band being fabricated from a flexible material and defining first and second edge portions for being positioned on opposite sides of the blood-pressure cuff as the blood-pressure cuff is received around the appendage, at least said first edge portion being provided with a draw member for drawing together said flexible material of said top band proximate said first edge portion and for biasing said first edge portion toward the appendage of the patient to prohibit contaminants from being communicated between said first edge portion and the appendage of the patient, whereby said top band forms a bloused protective barrier over the blood-pressure cuff which accommodates expansion of the blood-pressure cuff during use.

2. The blood-pressure cuff cover of claim 1 wherein said second edge portion is provided with a draw member for drawing together said flexible material of said top band proximate said second edge portion and for biasing said second edge portion toward the appendage of the patient to prohibit contaminants from being communicated between said second edge portion and the appendage of the patient.

3. The blood-pressure cuff cover of claim 2 wherein said draw members define lengths of elastic material secured along at least a substantial portion of the lengths of said first and second edge portions of said top band.

4. The blood-pressure cuff cover of claim 3 wherein said lengths of elastic material comprise elastic tape provided on at least an upper surface with an adhesive for securing said elastic tape to said top band of said cover.

5. The blood-pressure cuff cover of claim 2 wherein each said first and second edge portion of said top band defines an opening extending along said first and second edge portion, and said draw members define draw strings slidably received in said openings of said first and second edge portions.

6. The blood-pressure cuff cover of claim 2 wherein said top band defines first and second end portions and wherein said first end portion is provided with a securing mechanism for securing said first end portion to an adjacent portion of said top band after said top band has been received about the appendage and the blood-pressure cuff, thereby securing said top band in position about the blood-pressure cuff.

7. The blood-pressure cuff cover of claim 2 wherein said top band is fabricated of a dissolvable, substantially fluid impervious material.

8. The blood-pressure cuff cover of claim 2 wherein each said first and second edge portion of said top band is provided with an absorbent band for being disposed between the operatively associated said first and second edge portion and the appendage for absorbing fluid contaminants and prohibiting such fluid contaminants from being communicated between said first and second edge portion and the appendage.

9. A blood-pressure cuff cover for protecting a blood-pressure cuff from contamination, said cover comprising:

a bottom band for being releasably received around the upper portion of the arm of a patient and about which the blood-pressure cuff is releasably received, whereby said bottom band forms a protective barrier between the arm and the blood-pressure cuff, said bottom band defining a width greater than the width of the blood-pressure cuff such that as the blood-pressure cuff is secured about said bottom band, said bottom band defines first and second marginal areas on opposite sides of the blood-pressure cuff;

a securing mechanism for securing said bottom band in position about the arm of the patient;

a top band for being releasably received about the arm of the patient and around the blood-pressure cuff secured about said bottom band, said top band being fabricated from a flexible material and defining first and second opposite edge portions for being positioned on opposite sides of the blood-pressure cuff as the blood-pressure cuff is received around said bottom band, said first and second opposite edge portions being provided with draw members for drawing together said flexible material of said top band proximate said first and second opposite edge portions and for biasing said first and second edge portions into contact with said first and second marginal areas, respectively, of said bottom band to prohibit contaminants from being communicated between said first and second edge portions and said first and second marginal areas, whereby said top band forms a protective barrier over the blood-pressure cuff; and a further securing mechanism for securing said top band in position about the blood-pressure cuff and said bottom band.

10. The blood-pressure cuff cover of claim 9 wherein said bottom band defines first and second end portions and defines a length sufficient to allow said bottom band to completely wrap around the arm of the patient with said first end portion overlapping said second end portion.

11. The blood-pressure cuff cover of claim 10 wherein said top band define first and second end portions and defines a length sufficient to allow said top band to completely wrap around the blood-pressure cuff secured to the appendage of the patient with said first end portion of said top band overlapping said second end portion of said top band.

12. The blood-pressure cuff cover of claim 11 wherein said securing mechanism for securing said bottom band in position about the arm of the patient includes an adhesive strip secured to and extending from said first end portion of said bottom band, and wherein said further securing mechanism includes a further adhesive strip secured to and extending from said first end portion of said top band.

13. A blood-pressure cuff cover for protecting a blood-pressure cuff from contamination, said cover comprising:

a bottom band for being releasably received around an appendage of a patient and about which the blood-pressure cuff is releasably received, whereby said bottom band forms a protective barrier between the appendage and the blood-pressure cuff, said bottom band defining first and second end portions, said first end portion of said bottom band being provided with a securing mechanism for securing said first end portion of said bottom band to an adjacent portion of said bottom band after said bottom band has been received about the appendage of the patient, thereby securing said bottom band in position about the appendage; and a top band for being releasably received about the appendage of the patient and around the blood-pressure cuff secured about said bottom band, said top band being fabricated from a flexible material and defining first and second opposite edge portions for being positioned on opposite sides of the blood-pressure cuff as the blood-pressure cuff is received around said bottom band, said first and second opposite edge portions being provided with draw members for drawing together said flexible material of said top band proximate said first and second opposite edge portions and for biasing said first and second edge portions toward the appendage of the patient to prohibit contaminants from being communicated between said first and second edge portions and the appendage of the patient, whereby said top band forms a bloused protective barrier over the blood-pressure cuff which accommodates expansion of the blood-pressure cuff during use, said top band defining first and second end portions, said first end portion of said top band being provided with a securing mechanism for securing said first end portion of said top band to an adjacent portion of said top band after said top band has been received about the appendage and the blood-pressure cuff, thereby securing said top band in position about the blood-pressure cuff.

14. The blood-pressure cuff cover of claim 13 wherein said draw members define elastic tape secured along at least a substantial portion of the length of said first and second edge portions of said top band, said elastic tape defining an upper surfaces provided with adhesive for securing said elastic tape to said top band of said cover.

15. The blood-pressure cuff cover of claim 13 wherein each said first and second edge portion of said top band defines an opening extending along said first and second edge portion, and said draw members define draw strings slidably received in said openings of said first and second edge portions.

16. The blood-pressure cuff cover of claim 13 wherein said bottom band defines a width greater than the width of the blood-pressure cuff such that as the blood-pressure cuff is secured about said bottom band, said bottom band defines first and second marginal areas on opposite sides of the blood-pressure cuff, and wherein said draw members bias said first and second edge portions of said top band into contact with said first and second marginal areas, respectively, of said bottom band whereby the blood-pressure cuff is enclosed within said protective cover.

17. The blood-pressure cuff cover of claim 13 wherein said bottom band is fabricated of two-ply material having a first layer of soft, absorbent material for engaging the appendage of the patient and a second layer of substantially fluid impervious flexible plastic film.

18. The blood-pressure cuff cover of claim 17 wherein said top band is fabricated of a dissolvable, substantially fluid impervious flexible plastic film.

19. The blood-pressure cuff cover of claim 16 wherein said bottom band and said top band are connected by at least one connecting member which extends between said first marginal area of said bottom band and said first edge portion of said top band.

* * * * *